United States Patent [19]

Weigert

[11] Patent Number: 5,237,088
[45] Date of Patent: Aug. 17, 1993

[54] TRANSFER HYDROGENATION OF NITRILES USING AMINE DONORS

[75] Inventor: Frank J. Weigert, Wilmington, Del.

[73] Assignee: E. I. Du Pont de Nemours and Company, Wilmington, Del.

[21] Appl. No.: 857,344

[22] Filed: Mar. 25, 1992

[51] Int. Cl.$^5$ .......................................... C07C 253/30
[52] U.S. Cl. ................................. 558/455; 558/467; 558/454; 558/452; 558/388
[58] Field of Search .............. 558/455, 467, 454, 452, 558/388

[56] References Cited

U.S. PATENT DOCUMENTS

| | | | |
|---|---|---|---|
| 2,208,598 | 7/1940 | Rigby | 260/464 |
| 2,257,814 | 10/1941 | Rigby | 260/464 |
| 3,322,815 | 5/1967 | Feldman et al. | 260/465.5 |
| 3,696,153 | 10/1972 | Kershaw et al. | 260/583 K |
| 3,891,707 | 6/1975 | Wadden | 260/583 K |
| 4,362,671 | 12/1982 | Diamond et al. | 260/465.5 R |
| 4,389,348 | 6/1983 | Diamond et al. | 260/465.5 R |
| 4,601,859 | 7/1986 | Galle et al. | 558/459 |
| 4,716,256 | 12/1987 | Johnson et al. | 585/274 |
| 4,906,783 | 3/1990 | Smiley | 564/492 |
| 5,151,543 | 9/1992 | Ziemecki | 558/459 |

FOREIGN PATENT DOCUMENTS

| | | |
|---|---|---|
| 681932 | of 1966 | Belgium . |
| 836938 | 4/1952 | Fed. Rep. of Germany . |
| 848654 | 9/1952 | Fed. Rep. of Germany . |
| 2248265 | 5/1975 | France . |
| 52-042804 | 4/1977 | Japan . |
| 1214035 | 11/1970 | United Kingdom . |

OTHER PUBLICATIONS

Organic Synthesis; Collective vol. 3, (1955), pp. 176–183.
Maves, F. et al., *J. Catl.*, 112, 145–156 (1988).
Medina, F. et al., *J. Mol. Catal.*, 68, L17–L20 (1991).
Besson, M. et al., *Bull. Soc. Chim. Fr.* 127, 5–12, 13–19 (1990).
Murahashi et al., *Tet. Lett.*, 48, 4235–4238 (1975).
Brieger, G. et al., *Chem. Rev.*, 74, 567–580 (1974).
Johnstone, R. et al., *Chem. Rev.*, 85, 129–170 (1985).
Yamazaki, S. et al., *Bull. Chem. Soc. Jpn.*, 63, 301–303 (1990).

*Primary Examiner*—Joseph Paul Brust

[57] ABSTRACT

A process for transfer hydrogenation of nitriles and amines wherein the amines are the hydrogen donors is disclosed.

11 Claims, No Drawings

TRANSFER HYDROGENATION OF NITRILES USING AMINE DONORS

FIELD OF THE INVENTION

This invention relates to a process for transfer hydrogenation of nitriles and amines wherein the amines are used as the hydrogen source.

BACKGROUND OF THE INVENTION

Transfer hydrogenation is a general class of reactions in which hydrogen atoms from one organic molecule (donor) are used to hydrogenate another (acceptor). Many donors and acceptors have been studied. Amines have been used as donors, but not to hydrogenate nitriles. Nitriles have been used as acceptors, but not from amine donors. Nitriles have been reduced to amines with hydrogen, and amines have been dehydrogenated to nitriles and hydrogen. The present invention involves the concept of using transfer hydrogenation to equilibrate hydrogens among nitriles and amines.

Two papers by M. Besson, et al., *Bull. Soc. Chim. Fr.*, 127, 5–12 (1990), and ibid., 13–19, describe catalytic hydrogenation of valeronitrile with Raney nickel. Their reactions were run in cyclohexane solvent with hydrogen, ammonia, and additives (pentylamine, hexylamine). They found that if the molar ratio of hexylamine/valeronitrile was greater than 0.3, hydrogenation was retarded. They also observed that hydrogen had a significant influence on the interaction of the amine with the metal surface because replacing hydrogen by nitrogen pressure gave only negligible amounts of dihexylimine and no dihexylamine was detected.

The hydrogenation of aliphatic dinitriles, NCRCN, is usually carried out to completion, i.e., with addition of 4 mol of hydrogen per mole of dinitrile, in order to prepare the corresponding diamines, $H_2NCH_2RCH_2NH_2$. These are used, among other applications, in production of various polyamides. For example, adiponitrile is hydrogenated to hexamethylenediamine, one of the two monomers required in the production of Nylon 6,6; methylglutaronitrile is hydrogenated to methylpentamethylenediamine and/or 3-methylpiperidine; and dodecanedinitrile is hydrogenated to dodecamethylenediamine. The transfer hydrogenation process of the claimed invention is useful for the commercial production of compounds used in the production of various polyamides.

SUMMARY OF THE INVENTION

The present invention comprises a process for transfer hydrogenation of nitriles and amines comprising reacting, in the absence of hydrogen gas, a nitrile of formula $R^1CN$ with an amine of formula $R^2CH_2NH_2$ and a Raney nickel catalyst, wherein $R^1$ and $R^2$ are each independently $C_1$ to $C_{17}$ linear alkyl; $X—(CH_2)_y—$ wherein y is an integer of 3 to 16 and X is NC— or $H_2NCH_2—$; $(CH_2)_kN(CH_3)_2$ wherein k is 2 to 17; $—(CH_2)_mC_6H_5$ wherein m is 1 to 17; $—(CH_2)_nNH(CH_2)_{n+1}NH_2$ wherein n is 3 to 11; or $—(CH_2)_pH(CH_2)_pCN$ wherein p is 3 to 11; to generate the products $R^2CN$ and $R^1CH_2NH_2$ wherein $R^1$ and $R^2$ are as previously defined. More specifically, this invention describes a process for the transfer hydrogenation of nitriles and amines comprising reacting, in the absence of hydrogen gas, adiponitrile, hexamethylenediamine, and a Raney nickel catalyst to generate aminocapronitrile.

DETAILED DESCRIPTION OF THE INVENTION

This invention provides a process for the Raney nickel catalyzed transfer hydrogenation between amines (donors) and nitriles (acceptors) to generate a nitrile from the amine and an amine from the nitrile according to the following reaction:

$$R^1CN + R^2CH_2NH_2 \rightleftharpoons R^1CH_2NH_2 + R^2CN$$

wherein $R^1$ and $R^2$ are each independently defined as above.

The donors useful in the process of the present invention are selected from mono-, di-, or triamines of the formula $R^2CH_2NH_2$. The acceptors in said process are selected from mono- or dinitriles of the formula $R^1CN$ wherein $R^1$ and $R^2$ are each independently $C_1$ to $C_{17}$ linear alkyl; $X—(CH_2)_y—$ wherein y is an integer of 3 to 16 and X is NC— or $H_2NCH_2—$; $—(CH_2)_kN(CH_3)_2$ wherein k is 2 to 17; $—(CH_2)_mC_6H_5$ wherein m is 1 to 17; $—(CH_2)_nNH(CH_2)_{n+1}NH_2$ wherein n is 3 to 11; or $—(CH_2)_pNH(CH_2)_pCN$ wherein p is 3 to 11.

Preferred donors are amines wherein $R^2$ is $C_3$ to $C_{16}$ alkylamino or $—(CH_2)NH(CH_2)_nNH_2$. Preferred acceptors are nitriles wherein $R^1$ is $C_3$ to $C_{16}$ alkylnitrile or $—(CH_2)_pNH(CH_2)_pCN$. Especially preferred donor and acceptor are, respectively, hexamethylenediamine and adiponitrile. The donors and acceptors useful herein are easily prepared by methods known in the art or purchased commercially.

The mole ratio of donor to acceptor used in the process of the present invention is from about 10:1 to about 1:10. Preferably a mole ratio of 1 to 1 is employed.

Catalysts found to be active in the present invention comprise Raney nickels. These can be purchased commercially or prepared by methods known to those skilled in the art. The amount of catalyst employed is typically 0.1:1 to 10:1, preferably 0.5:1 to 2:1, compared to the amount of donor and acceptor. All Raney nickels as prepared contain surface hydrogen. This hydrogen rapidly reduces nitriles to amines. Thus, the initial amine formed from nitrile may result from a stoichiometric reaction of Raney nickel hydrogen with nitrile, rather than by transfer hydrogenation. Hydrogenation of 6-aminocapronitrile can produce 1,6-hexamethylenediamine but not adiponitrile. Therefore, adiponitrile formed from the reaction of 6-aminocapronitrile and Raney catalysts (e.g., see Examples 11–21) must arise from a transfer hydrogenation process. There may be more 1,6-hexamethylenediamine than adiponitrile, but the mere presence of adiponitrile from 6-aminocapronitrile disproportionation indicates that transfer hydrogenation has occurred.

The transfer hydrogenation reaction of the present invention can be run without any solvent by just mixing the amine, nitrile, and catalyst. However, the rate is greatly improved when an effective solvent is present. Examples 22–46 show the results of equilibrating hexanenitrile and octylamine using a Raney nickel catalyst in various solvents as summarized in Table 2.

Two criteria were used to judge the effectiveness of a solvent. First, the rate of transfer hydrogenation is faster than without solvent present. Second, the product amine and nitrile are formed in essentially equal amounts. Chelating, hard ligands were found to be outstanding solvents for transfer hydrogenation. Other solvents, such as ethanol, outcompete the amine as donor in the reaction, and therefore little nitrile was produced.

The preferred solvents of the process of the present invention are non-interfering ethers (e.g., are not hydrogen donors), including ethers with one or more ether linkages arranged in a straight chain or cyclic fashion. Examples include p-dioxane, tetrahydrofuran, tert-butyl methyl ether, 1,2-dimethoxyethane, benzodioxane, diethyl ether, m-dioxane, veratrole, and tetraglyme. Other solvents are hydrocarbons (e.g., toluene, n-octane), or cyclic tertiary amines (e.g., 4-methylmorpholine). Interfering solvents are those that participate in the reaction, i.e., contain groups that are oxidized, reduced, or reactive in some other way under the reaction conditions. Examples of solvents are given, but are not limited to, those shown in Table 2. Preferred as solvents are dioxane or 1,2-dimethoxyethane.

The transfer hydrogenation reaction can be run at temperatures ranging from about 20° C. to about 200° C. The preferred temperature range is from about 80° C. to about 160° C. Especially preferred is the reflux temperature of the solvent. For the preferred solvents of the invention, the reflux temperature is within the preferred temperature range of 80° C. to 160° C. Examples 47–52 illustrate a non-limiting range of temperatures.

The transfer hydrogenation reaction is most conveniently run at atmospheric pressure. Oxygen and other oxidative gases must be excluded, and therefore, the reaction is most conveniently run in the presence of an inert gas, such as the noble gases of Group VIIIA of the Periodic Table of Elements. Preferably the reaction is run under a nitrogen gas atmosphere.

A preferred embodiment of the process of the present invention is the transfer of hydrogen from a diamine donor (i.e., wherein $R^2$ is $H_2NCH_2(CH_2)_y$ or $-(CH_2)_nNH(CH_2)_{n+1}NH_2$ wherein n is 3 to 11) to a dinitrile acceptor (i.e., wherein $R^1$ is $NC(CH_2)_y$ or $-(CH_2)_pNH(CH_2)_pCN$ wherein p is 3 to 11) to produce monoaminonitriles. An example of this preferred embodiment is the reaction of 1,6-hexamethylenediamine with adiponitrile to form 6-aminocapronitrile according to the following reaction:

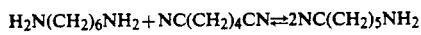

$$H_2N(CH_2)_6NH_2 + NC(CH_2)_4CN \rightleftharpoons 2NC(CH_2)_5NH_2$$

As can be seen from this reaction, the diamine is dehydrogenated and the hydrogen atoms transferred to the dinitrile. In this case, both the diamine and the dinitrile have the same number of carbon atoms arranged in a linear chain, so two moles of one product are produced from one mole of each of the reactants. If the diamine and dinitrile had different numbers of carbon atoms or different arrangements of the atoms, one mole of each of two different monoaminonitriles would have been produced. The product in this preferred embodiment can be easily distilled and separated from unreacted starting materials, which can be recycled. The process is efficient, economic, and avoids the use of hydrogen gas, which is potentially explosive and also adds cost to the process. The starting materials, 1,6-hexamethylenediamine and adiponitrile, are well-known and are commercially available.

The product, 6-aminocapronitrile, among other applications, can be polymerized in the presence of water to prepare nylon 6, which represents about half of all nylon fiber production worldwide. Similarly, the other aminonitriles, which can be prepared using the process of this invention, can be polymerized to form other polyamides. The reaction may be run in the reverse direction, e.g., 6-aminocapronitrile, subjected to the present process conditions, will equilibrate, producing 1,6-hexamethylenediamine and adiponitrile, which are used as intermediates in the preparation of nylon 66. Other amines and nitriles that can be provided by the invention are also useful as synthetic intermediates. For example, nitriles are easily converted by well-known techniques into carboxylic acid derivatives.

The following examples illustrate the process of the present invention, but are not intended to limit it in any manner.

EXAMPLES

Standard Disproportionation Procedure

A 100 mL three-neck round-bottom flask was equipped with a magnetic stirrer and water-cooled condenser. The flask was purged with $N_2$, and solvent (optional) and reactants were added. The catalyst slurry was taken up in a 10 cc syringe. The syringe was inverted, the metal catalyst was allowed to settle (required only a few seconds), and the plunger was then depressed to remove most of the water from the slurry. The combined syringe and slurry were weighed, the catalyst added to the flask, and the syringe re-weighed in order to calculate the net weight of the wet catalyst added. A $t_0$ (time=0) sample was taken for GC (gas chromatographic) analysis, and the flask immediately immersed in an oil bath, which had been preheated to the desired temperature, and the clock started. Periodically, the time was noted and samples were withdrawn for GC analysis.

Gas chromatography was done with a 30 m (length), DB-5 capillary column. The temperature program involved an initial hold of 4 min at 75° C. followed by a ramp of 35°/min to 220° C. and a 4 min hold at that temperature. Representative retention times (in min) are 1,6-hexamethylenediamine=6.0, 6-aminocapronitrile=6.4, and adiponitrile=6.8.

EXAMPLE 1

Using the Standard Disproportionation Procedure, 3.2 g of hexanenitrile was reacted with 3.1 g octylamine; 3.4 g of Raney nickel (Davison 2400) available from W. R. Grace & Co., Davison Chemical Division, P.O. Box 2117, Baltimore, Md., 21203, was used and the temperature was 100° C. The product analysis after 45 min showed (from GC area %): hexylamine 8.1%, hexanenitrile 31%, octylamine 48%, and octylnitrile 2.7%.

EXAMPLE 2

Using the Standard Disproportionation Procedure, 10 cc of a 1:1 molar mixture of adiponitrile (ADN) add 1,6-hexamethylenediamine (HMD) was allowed to react; 1.22 g of Raney nickel (Davison 2400) was used and the temperature was 100° C. The product analysis after 8280 min showed (from normalized GC area %): HMD 42%, 6-aminocapronitrile 15.6%, ADN 42%.

EXAMPLE 3

Using the Standard Disproportionation Procedure, 2.98 g dodecanedinitrile (DDDN) was reacted with 2.96 g 1,12-diaminododecane (DADD); 1.22 g of Raney nickel (Davison 2400) was used and the temperature was 100° C. The product analysis after 45 min showed (from normalized GC area %): DADD 41%, 12-aminododecanenitrile 12.4%, DDDN 46%.

EXAMPLE 4

Using the Standard Disproportionation Procedure, 3 cc hexylamine was reacted with 3 cc benzylcyanide; 4.4 g of Raney nickel (Grace LM112W) available from W. R. Grace & Co., 55 Hayden Ave., Lexington, Mass., 02173, was used and the temperature was 100° C. The product analysis after 60 min showed (from GC area %): hexylamine 41%, hexanenitrile 2.0%, benzylamine 4.7%, and benzylnitrile 52%.

EXAMPLE 5

Using the Standard Disproportionation Procedure, 3 cc hexylamine was reacted with 3 cc propionitrile; 3.6 g of Raney nickel (Grace LM112W) was used and the temperature was 100° C. The product analysis after 60 min showed (from GC area %): hexylamine 53%, hexanenitrile 11%, propylamine 7.2%, propionitrile 29%.

EXAMPLE 6

A 10 cc shaker tube was flushed with $N_2$ and charged with a slurry of 2.7 g Raney nickel (Grace LM112W) in 4 cc of an equimolar mixture of hexylamine and acetonitrile. The tube was closed, cooled to −78° C. and briefly evacuated. It was heated at 100° C. for 2 h, then cooled to room temperature and vented. Analysis by GC showed the absence of hexanenitrile in the starting solution and presence of equal amounts of hexanenitrile and ethylamine in the product.

EXAMPLE 7

Using the Standard Disproportionation Procedure, 3 g octadecylamine was reacted with 3 g hexanenitrile; 4.6 g of Raney nickel (Grace LM112W) was used and the temperature was 100° C. The product analysis after 60 min showed (from GC area %): octadecylamine 44%, octadecanenitrile 6.3%, hexylamine 5.1%, hexanenitrile 45%.

EXAMPLE 8

Using the Standard Disproportionation Procedure, 5 cc octylamine was reacted with 5 cc dimethylaminopropionitrile; 4.4 g of Raney nickel (Grace LM112W) was used and the temperature was 100° C. The product analysis after 60 min showed (from GC area %): octylamine 54%, octanenitrile 5.7%, dimethylaminopropylamine 4.2%, dimethylaminopropionitrile 36%.

EXAMPLE 9

Using the Standard Disproportionation Procedure, 5 cc dimethylaminopropylamine was reacted with 3 cc hexanenitrile; 3.8 g of Raney nickel (Davison 2400) was used and the temperature was 100° C. The product contained dimethylaminopropionitrile and hexylamine.

EXAMPLE 10

Using the Standard Disproportionation Procedure, 1 g bishexamethylenetriamine was reacted with 5 cc hexanenitrile in 20 cc dioxane solvent; 2.6 g of Raney nickel (Davison 2400) was used and the temperature was 100° C. The product analysis after 60 min showed (from GC area %) of the six-carbon specie: hexylamine 8.4%, hexanenitrile 92%; of the twelve-carbon specie: bis(hexamethylene)triamine 54%, 5-cyanopentylhexamethylenediamine 40%, bis(5-cyanopentyl)amine 5.3%.

EXAMPLES 11–21

The series of Raney nickel catalysts shown in Table 1 was tested using the Standard Disproportionation Procedure. In these cases, the equilibration was run in the reverse direction, starting with 6-aminocapronitrile (AMCN) and allowing it to disproportionate to hexamethylenediamine (HMD) and adiponitrile (ADN). The reaction was run using 10 cc of AMCN and the catalysts and amounts shown in Table 1 at a temperature of 100° C. A sample was taken after 60 min for GC analysis.

TABLE 1

| Catalysts Tested for AMCN Disproportionation | | | | |
|---|---|---|---|---|
| Ex. | Catalyst | Weight (g) | HMD (mol %) | AMCN (mol %) | ADN (mol %) |
| 11 | RaNi Davison 2400 | 2.9 | 3.6 | 92 | 4.5 |
| 12 | RaNi Strem* 20042-S2 | 2.2 | 1.7 | 97 | 1.4 |
| 13 | RaNi Grace 111RW | 3.7 | 3.7 | 94 | 2.7 |
| 14 | RaNi Grace M113W (Ni, Fe) | 4.0 | 3.4 | 94 | 2.3 |
| 15 | RaNi Grace LM112W (Ni, Cr, Fe) | 3.9 | 5.9 | 91 | 3.0 |
| 16 | RaNi Grace N113W 10% Co | 3.5 | 1.6 | 97 | 1.5 |
| 17 | RaNi Davison 2400 (Cr) | 2.5 | 3.2 | 96 | 1.3 |
| 18 | RaNi Mo/Fe/Cr promoted | 1.5 | 1.7 | 96 | 1.0 |
| 19 | RaNi Davison 2800 | 1.2 | 0.6 | 99 | 0.4 |
| 20 | RaNi Davison 3100 (Mo) | 2.3 | 0.9 | 97 | 0.4 |
| 21 | RaNi Davison 4200 | 3.1 | 1.0 | 97 | 0.6 |

*Available from Strem Chemicals, 7 Mulliken Way, Newburyport, MA, 01950.

EXAMPLES 22–46

The effect of solvent on the transfer hydrogenation reaction was tested using the Standard Disproportionation Procedure. A mixture of 2 cc hexylamine/octylnitrile (ca. 50% by volume of each), 20 cc of the various solvents shown in Table 2, and 3.5 g Raney nickel (Grace LM112W) was allowed to react at 85° C. under an $N_2$ atmosphere. After 30 min, a sample was taken for GC analysis. Product data is listed in Table 2 in mol %.

Examples 22–46 were all conducted according to this procedure, with the following exceptions. Example 23 was run for 60 min rather than 30 min. Example 30 was run at reflux (ca. 55° C.) rather than at 85° C. Examples 33, 34, 35, and 36 were run at room temperature (ca. 5° C.). Examples 45 and 46 were run at 100° C., and the Raney nickel catalyst used was Davison 2400 (2.9 g in Example 45 and 2.7 g in example 46).

TABLE 2

| Solvent Effect on Transfer Hydrogenation | | | | | |
|---|---|---|---|---|---|
| | | mol Percent | | | |
| | | Hexyl | | Octyl | |
| Example | Solvent | amine | nitrile | amine | nitrile |
| 22 | p-Dioxane | 21.6 | 23.9 | 32.0 | 22.5 |
| 23 | p-Dioxane | 26.0 | 20.4 | 28.5 | 25.0 |
| 24 | Ethanol | 54.7 | 9.8 | 25.3 | 10.2 |
| 25 | Ethyl acetate | 20.1 | 26.5 | 43.0 | 10.5 |
| 26 | tert-Butanol | 11.9 | 33.5 | 46.7 | 7.9 |
| 27 | Pyridine | 15.0 | 30.3 | 44.8 | 9.9 |
| 28 | Tetrahydrofuran | 15.3 | 30.6 | 44.4 | 9.8 |
| 29 | Triethylamine | 11.1 | 32.7 | 46.7 | 9.5 |
| 30 | tert-Butyl methyl ether | 8.4 | 35.7 | 52.7 | 3.2 |
| 31 | 1,2-Dimethoxyethane | 23.3 | 21.8 | 32.4 | 22.4 |
| 32 | Benzodioxane | 12.2 | 30.7 | 47.5 | 9.6 |

TABLE 2-continued

Solvent Effect on Transfer Hydrogenation

| | | mol Percent | | | |
|---|---|---|---|---|---|
| | | Hexyl | | Octyl | |
| Example | Solvent | amine | nitrile | amine | nitrile |
| 33 | Diethyl ether | 9.8 | 33.8 | 51.7 | 4.7 |
| 34 | Tetrahydrofuran | 9.2 | 34.5 | 50.7 | 5.6 |
| 35 | 1,2-Dimethoxyethane | 3.8 | 39.3 | 48.4 | 8.5 |
| 36 | p-Dioxane | 3.0 | 42.3 | 51.7 | 3.1 |
| 37 | m-Dioxane | 24.0 | 28.5 | 33.1 | 14.4 |
| 38 | 4-Methylmorpholine | 19.4 | 25.2 | 37.4 | 17.9 |
| 39 | 1,4-Dimethylpiperazine | 15.3 | 29.9 | 43.1 | 11.7 |
| 40 | Morpholine | 8.5 | 36.3 | 53.2 | 2.0 |
| 41 | Veratrole | 26.9 | 26.9 | 33.8 | 12.4 |
| 42 | Tetraglyme | 31.9 | 22.5 | 26.7 | 19.0 |
| 43 | 2-Methyl tetrahydrofuran | 31.6 | 22.1 | 33.5 | 12.8 |
| 44 | Ethylenediamine | 4.5 | 50.1 | 44.3 | 1.2 |
| 45 | Toluene | 9.6 | 38.5 | 69.0 | 2.9 |
| 46 | n-Octane | 10.5 | 33.7 | 52.6 | 3.2 |

EXAMPLES 47-52

The effect of temperature on the transfer hydrogenation reaction was tested using the Standard Disporportionation Procedure. In this case, the equilibration was run in the reverse direction, starting with 6-aminocapronitrile (AMCN) and allowing it to disproportionation to hexamethylenediamine (HMD) and adiponitrile (ADN). The reaction was run using 10 cc of AMCN and the catalyst was Raney nickel (Davison 2400); amounts of catalyst and temperatures are shown in Table 3. A sample was taken after 60 min for GC analysis. Product analysis for Examples 47-50 is given in area % (normalized), and for Examples 51-52 in mole % (normalized). The difference between the sums and 100% represents byproducts.

TABLE 3

Temperature Range for AMCN Disproportionation

| Example | Temp °C. | Cat Wt g | HMD | AMCN | ADN |
|---|---|---|---|---|---|
| 47 | 82 | 4.5 | 5.1 | 91 | 4.1 |
| 48 | 109 | 2.9 | 3.8 | 92 | 4.3 |
| 49 | 129 | 2.9 | 11.3 | 84 | 5.1 |
| 50 | 100 | 2.5 | 3.3 | 95 | 1.2 |
| 51 | 100 | 3.5 | 3.0 | 95 | 1.7 |
| 52 | 160 | 3.8 | 6.0 | 79 | 4.1 |

What is claimed is:

1. A process for transfer hydrogenation of nitriles with amines comprising, reacting, at a temperature of from about 20° C. to about 200° C., in the absence of hydrogen gas, a nitrile of formula $R^1CN$ with an amine of formula $R^2CH_2NH_2$ and a Raney nickel catalyst, wherein $R^1$ and $R^2$ are each independently $C_1$ to $C_{17}$ linear alkyl; $X-(CH_2)_y-$ wherein y is an integer of 3 to 16 and X is NC— or $H_2NCH_2-$; $-(CH_2)_kN(CH_3)_2$ wherein k is 2 to 17; $-(CH_2)_mC_6H_5$ wherein m is 1 to 17; $-(CH_2)_nNH(CH_2)_{n+1}NH_2$ wherein n is 3 to 11; or $-(CH_2)_pNH(CH_2)_pCH$ wherein p is 3 to 11;

to generate the products $R^2CH$ and $R^1CH_2NH_2$ wherein $R^1$ and $R^2$ are as defined above.

2. The process of claim 1 wherein $R^1$ is $NC(CH_2)_y-$ or $-(CH_2)_pNH(CH_2)_pCN$.

3. The process of claim 1 wherein $R^2$ is $H_2NCH_2(CH_2)_y-$ or $-(CH_2)_nNH(CH_2)_{n-1}NH_2$.

4. The process of claim 1 wherein $R^1$ is $NC(CH_2)_y-$ and $R^2$ is $H_2NCH_2(CH_2)_y-$.

5. The process of claim 1 wherein the product is one or more aminonitrile compounds.

6. The process of claim 1 conducted at a temperature of from about 80° C. to about 160° C.

7. The process of claim 1 conducted in a solvent comprising an ether, hydrocarbon, or cyclic tertiary amine other than triethylamine.

8. The process of claim 7 wherein the solvent comprises dioxane or dimethoxyethane.

9. The process of claim 1 conducted in an inert atmosphere.

10. The process of claim 9 wherein the atmosphere is nitrogen.

11. A process for the transfer hydrogenation of nitriles and amines comprising reacting, in the absence of hydrogen gas, adiponitrile, 1,6-hexamethylenediamine, and a Raney Ni catalyst to generate 6-aminocapronitrile.

* * * * *